various embodiments, the formulation may be in the form of, e.g., an aqueous solution or suspension, an ingestible solid or liquid form, or a topical preparation, and may be used to treat a variety of diseases and conditions responsive to the combination.

(12) United States Patent
Bretz

(10) Patent No.: US 11,235,012 B2
(45) Date of Patent: Feb. 1, 2022

(54) COMBINATION AND USE OF RED PROPOLIS AND RED ALGAE

(71) Applicant: Walter A. Bretz, Nevada City, CA (US)

(72) Inventor: Walter A. Bretz, Nevada City, CA (US)

( * ) Notice: Subject to any disclaimer, the term of this patent is extended or adjusted under 35 U.S.C. 154(b) by 18 days.

(21) Appl. No.: 16/916,743

(22) Filed: Jun. 30, 2020

(65) Prior Publication Data

US 2021/0401911 A1  Dec. 30, 2021

(51) Int. Cl.

| | | |
|---|---|---|
| *A61K 36/04* | (2006.01) | |
| *A61K 9/00* | (2006.01) | |
| *A61K 47/44* | (2017.01) | |
| *A61K 47/38* | (2006.01) | |
| *A61K 47/10* | (2017.01) | |
| *A61K 47/18* | (2017.01) | |
| *A61K 47/26* | (2006.01) | |
| *A61K 47/36* | (2006.01) | |
| *A61K 8/9717* | (2017.01) | |
| *A61K 8/98* | (2006.01) | |
| *A61Q 1/06* | (2006.01) | |
| *A61Q 1/10* | (2006.01) | |
| *A61Q 1/08* | (2006.01) | |
| *A61Q 1/02* | (2006.01) | |
| *A61K 35/644* | (2015.01) | |
| *A61K 36/28* | (2006.01) | |

(52) U.S. Cl.
CPC ........... *A61K 36/04* (2013.01); *A61K 8/9717* (2017.08); *A61K 8/988* (2013.01); *A61K 9/0043* (2013.01); *A61K 9/0053* (2013.01); *A61K 35/644* (2013.01); *A61K 36/28* (2013.01); *A61K 47/10* (2013.01); *A61K 47/183* (2013.01); *A61K 47/26* (2013.01); *A61K 47/36* (2013.01); *A61K 47/38* (2013.01); *A61K 47/44* (2013.01); *A61Q 1/02* (2013.01); *A61Q 1/06* (2013.01); *A61Q 1/08* (2013.01); *A61Q 1/10* (2013.01)

(58) Field of Classification Search
CPC ....... A61K 36/04; A61K 35/644; A61K 8/988
See application file for complete search history.

(56) References Cited

U.S. PATENT DOCUMENTS

| | | | |
|---|---|---|---|
| 10,285,929 B1 | 5/2019 | Bretz | |
| 2012/0177806 A1* | 7/2012 | Kraan | A23K 40/25 426/635 |

FOREIGN PATENT DOCUMENTS

CN  108619495 A  10/2018

OTHER PUBLICATIONS

Rufatto, L. C., et al. "Red propolis: Chemical composition and pharmacological activity" Asian Pac J Trap Biomed 2017; 7(7): 591-598 (Year: 2017).*
Extended European Search Report from corresponding European Patent Application No. 21182621.9, dated Nov. 24, 2021, 11 pages.
Anonymous, "Propargile—Holistica International," May 1, 2020, XP055860991, 3 pages.
Aroma-Zen, "Capsules P.A.P.A. Propolis—clay—pollen—algae—Propolia—80 capsules," Jun. 20, 2017, XP055860986, 2 pages.
Freires et al., "A pharmacological perspective on the use of Brazilian Red Propolis and its isolated compounds against human diseases," European Journal of Medicinal Chemistry, 110:267-79, Jan. 20, 2016, XP029415635, 13 pages.
Aslam et al., "Growth-inhibitory effects of a mineralized extract from the red marine algae, Lithothamnion calcareum, an Ca2+-sensitive and Ca2+-resistant human colon carminoma cells," Cancer Letters, 283:186-92, Oct. 8, 2009, XP026421124, 7 pages.
Reis et al., "Evaluation of the antioxidant profile and cytotoxic activity of red propolis extracts from different regions of northeastern Brazil obtained by conventional and ultrasound-assisted extraction," PLOS One, vol. 14, No. 7, Jul. 5, 2019, XP055862026, 27 pages.
McClintock et al., "Calcium-Induced Differentiation of Human Colon Adenomas in Colonoid Culture: Calcium Alone versus Calcium with Additional Trace Elements," Cancer Prev. Res., 11:413-27, Nov. 16, 2021, XP055862093, 17 pages.

\* cited by examiner

*Primary Examiner* — Andrew S Rosenthal
(74) *Attorney, Agent, or Firm* — Hoffman Warnick LLC

(57) ABSTRACT

Formulations comprising a combination of red propolis and red algae, e.g., *L. calcareum*, as active ingredients, and methods of treatment using the same are provided herein. In various embodiments, the formulation may be in the form of, e.g., an aqueous solution or suspension, an ingestible solid or liquid form, or a topical preparation, and may be used to treat a variety of diseases and conditions responsive to the combination.

20 Claims, 5 Drawing Sheets

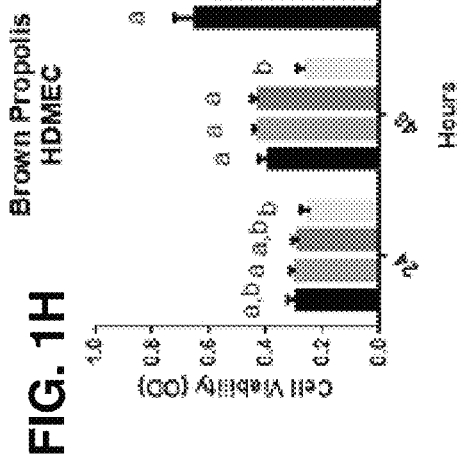
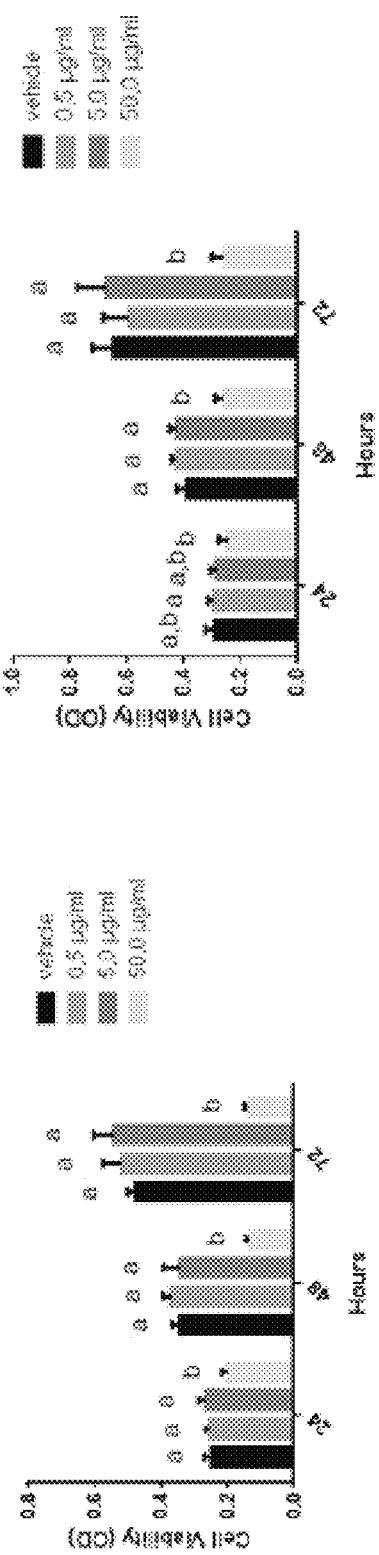
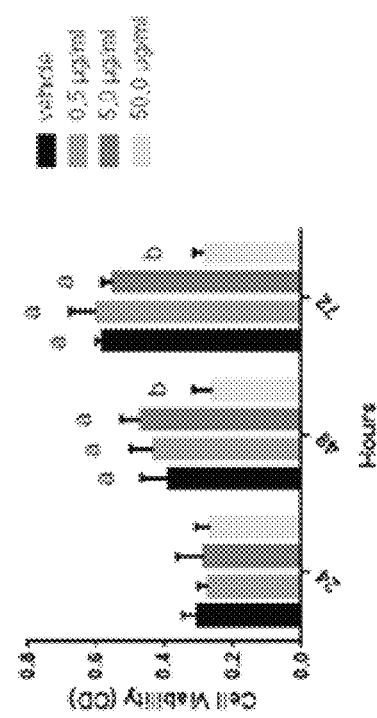
FIG. 1G
FIG. 1H
FIG. 1I

COMBINATION AND USE OF RED PROPOLIS AND RED ALGAE

BACKGROUND OF THE INVENTION

The invention relates generally to formulations and methods of treatment for diseases and conditions improved by one of antioxidant activity, antibacterial activity, antiviral activity, antifungal activity, anti-cancer activity, or immunomodulatory activity. More particularly, the invention relates to formulations comprising a combination of red propolis and red algae, e.g., *Lithothamnium calcareum*, as active ingredients, and their use in the treatment of diseases and conditions responsive to the combination.

Western diets are linked to multiple health problems such as obesity, inflammatory bowel disease, cardiovascular disease, and metabolic diseases. Deficiencies in magnesium and calcium have been linked with an increased risk of malnutrition, cardiovascular disease, type 2 diabetes, decreased bone mineral density, and some cancers. Evidence suggests that dietary supplementation with these nutrients plays a role in the process of healthy aging. In addition to these deficiencies, western diets can also modulate the host microbiome and particularly, the gut microbiome, with significant detriment to health. Methods and treatments are needed to address these health concerns.

Propolis is a resinous substance synthetized by bees in the construction, maintenance and defense of their hives. Owing to its bioactive constituents, propolis is understood to possess protective immune defense and antioxidant properties. The composition of propolis varies seasonally and by geographical location of origin. Propolis may include compounds such as, e.g., phenolic acids, flavonoids, esters, diterpenes, sesquiterpenes, lignans, aromatic aldehydes, alcohols, amino acids, fatty acids, vitamins, minerals, and others. Propolis has been investigated for the provision of proposed health benefits and properties including anti-microbial properties, antioxidant properties, anti-cancer properties, wound healing benefits, immunomodulation benefits, and is widely used in the cosmetic industry. Propolis has been used in the treatment of upper respiratory tract infections, common cold, and flu-like infections, as well as dermatological preparations useful in wound healing, treatment of burns, acne, herpes simplex and genitalis, and neurodermatitis.

A number of variations of propolis are known, including brown, green, black, white, and red propolis. A relatively recent subject of investigational interest, red propolis has been characterized and found to contain different constituent compounds having antimicrobial, anti-inflammatory, anti-parasitic, anti-protozoal, anti-tumorigenic, antioxidant, immunomodulatory, and metabolic activity. Red propolis is a resin exuded from wounds caused by insects feeding on stems of a woody climber or prostrate plant of the genus *Dalbergia*. The species occurs on restingas (vegetation growing on sandy soil close to the sea) and mangroves. The species has been referred to as *Dalbergia ecastophyllum*.

*Lithothamnium calcareum* (*L. calcareum*, abbreviated LC herein), also known as *Phymatolithon calcareum*, is a marine-derived multi-mineral extract obtained from the skeletal remains of the red marine algae. The algae thrive in the Atlantic Ocean and may be found, for example, off the southwest coast of Ireland, northwest coast of Iceland, northeast coast of Brazil, and northwest coast of France. Major components of this multi-mineral extract include calcium (about 12-20% by weight), magnesium (about 1-4% by weight), and measurable levels of 74 other trace elements, including phosphorus which enhances bioavailability. U.S. Pat. No. 10,285,929, which is incorporated by reference herein, discloses the use of LC-containing compositions to increase salivary secretory Immunoglobulin A (SIgA) in a mammal, e.g., a human. SIgA is the dominant immunoglobulin produced by secretions originating from the epithelial lining that bathe mucosal surfaces (e.g., oral, respiratory, intestinal, and reproductive). SIgA plays a critical role in guarding against microbial invasion by inhibiting the attachment of pathogenic microbes to mucosal surfaces. SIgA levels are generally undetectable at birth, elevate rapidly during the first months of life, and continue to increase until stabilizing during childhood (e.g. ages 5-7). SIgA levels may decrease for a variety of reasons including but not limited to aging (e.g., later in adulthood), the presence of stress related conditions, and nutritional deficiencies. Decreases in SIgA pose significant risk, given its critical importance in mucosal resistance to infection.

Cancerous cells and adenomatous polyp cells, which are potential precursors of colorectal cancer, have characteristic features including increased proliferative activity with concomitant reduced differentiation in phenotype and reduced apoptotic ability. LC multi-mineral extracts have also been shown to inhibit polyp formation in animal models and to ameliorate the spontaneous development of colitis and the severity of disease in IL-10 knockout mice on a C57BL/6J background, and to reduce colonic inflammation and polyp formation in the gastrointestinal tract of mice fed a high-fat diet. Moreover, combination therapies that include LC have shown to important regulators of cell growth in human cancer cell lines.

BRIEF DESCRIPTION OF THE INVENTION

In a first aspect of the invention, a formulation is provided, comprising a combination of red propolis and *L. calcareum* as active ingredients. The formulation may be in the form of, e.g., an aqueous solution or suspension for use as an oral rinse or an oral or nasal spray, an ingestible solid or liquid form, or a topical preparation.

In a second aspect of the invention, a method is provided for treating a mammalian subject in need of treatment for a disease or condition responsive to a combination of *L. calcareum* and red propolis, the method comprising administering to the subject a formulation comprising the combination of red propolis and LC. The formulation may be in the form of, e.g., an aqueous solution or suspension for use as an oral rinse or an oral or nasal spray, an ingestible solid or liquid form, or a topical preparation, and the disease or condition responsive to the combination of LC and red propolis may be influenza; an upper or lower respiratory infection; oral cavity inflammation; pharynx inflammation, malnutrition, enhancement of immune system function, a gastric ulcer; colitis; gastritis; cancer, e.g., head and neck cancer, glioblastoma; melanoma; lung cancer; prostate cancer; bladder cancer; a wound; a flesh burn; acne; herpes simplex; herpes genitalis; neurodermatitis; aging skin; pigmented skin, e.g., dark spots; stretch marks; dry skin; or skin inflammation.

In a third aspect of the invention a process is provided for preparing an extract of red propolis, the process comprising: extracting a plurality of active compounds from homogenized red propolis in a hydro-alcoholic ethanol solution at 25-28 degrees Celsius, wherein the active compounds are isoprenylated benzophenones, pterocarpanes, and isoflavanes; and subjecting the homogenized material in the hydro-alcoholic ethanol solution to ultrasound for 2-3 hours.

These and other aspects, advantages and salient features of the invention will become apparent from the following detailed description, which, when taken in conjunction with the annexed figures, disclose embodiments of the invention.

BRIEF DESCRIPTION OF THE DRAWINGS

FIG. 1G is a bar chart illustrating the effect on HDMEC cell viability over time following administration of vehicle, 0.5 μg/ml, 5.0 μg/ml, and 50 μg/ml of red propolis, respectively.

FIG. 1H is a bar chart illustrating the effect on HDMEC cell viability over time following administration of vehicle, 0.5 μg/ml, 5.0 μg/ml, and 50 μg/ml of brown propolis, respectively.

FIG. 1I is a bar chart illustrating the effect on HDMEC cell viability over time following administration of vehicle, 0.5 μg/ml, 5.0 μg/ml, and 50 μg/ml of green propolis, respectively.

Figure 1A:
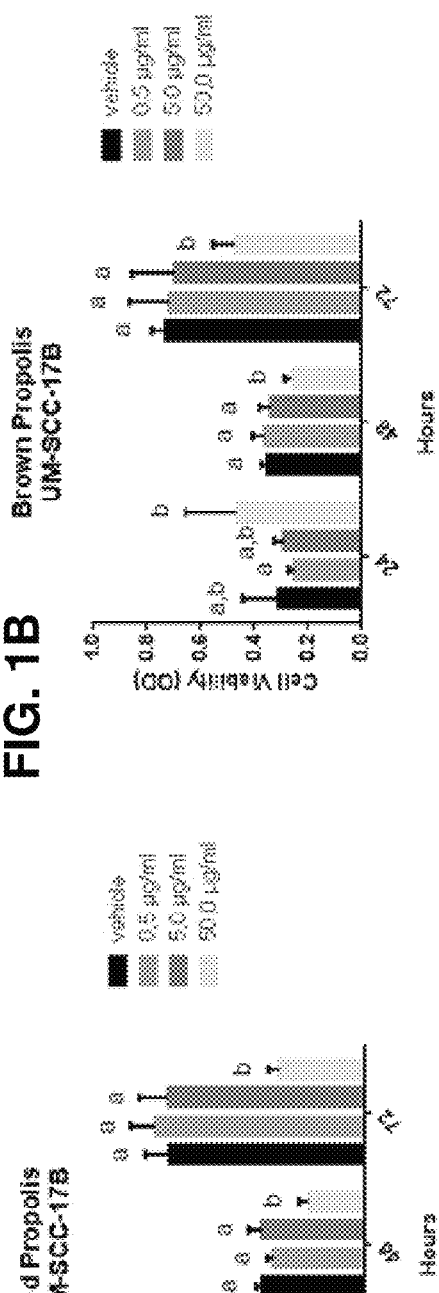
FIG. 1A is a bar chart illustrating the effect on UM-SCC-17B cell viability over time following administration of vehicle, 0.5 μg/ml, 5.0 μg/ml, and 50 μg/ml of red propolis, respectively.
Figure 1B:
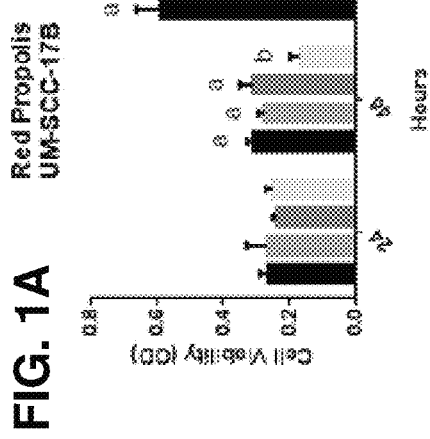
FIG. 1B is a bar chart illustrating the effect on UM-SCC-17B cell viability over time following administration of vehicle, 0.5 μg/ml, 5.0 μg/ml, and 50 μg/ml of brown propolis, respectively.
Figure 1C:
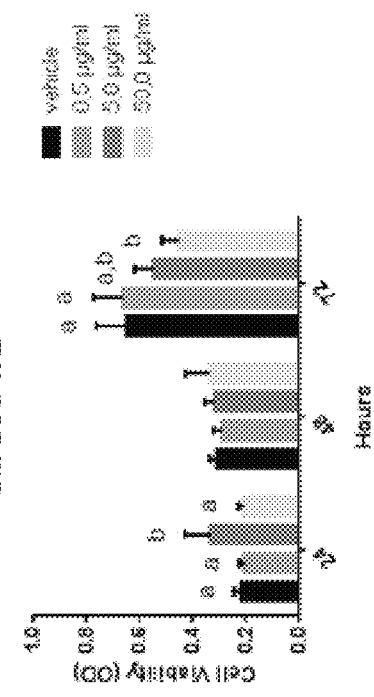
FIG. 1C is a bar chart illustrating the effect on UM-SCC-17B cell viability over time following administration of vehicle, 0.5 μg/ml, 5.0 μg/ml, and 50 μg/ml of green propolis, respectively.

The figures are intended to depict only typical aspects of the disclosure, and therefore should not be considered as limiting the scope of the disclosure.

DETAILED DESCRIPTION OF THE INVENTION

The present invention includes pharmaceutical, nutraceutical, and cosmetic formulations comprising a combination of red propolis and red algae, e.g., *L. calcareum* (LC). Such formulations may be used, for example, as an oral or nasal spray or rinse, an ingestible solid or liquid form, or a topical preparation. Also disclosed herein are methods of use of the novel formulations to provide a variety of health and medicinal benefits.

The combination of red propolis and LC offers a number of therapeutic and beneficial properties. For example, formulations containing the combination of red propolis and LC show antioxidant, antimicrobial, anti-inflammatory, anti-tumorigenic, and immunomodulatory activity, including, e.g., increasing levels of salivary secretory IgA. The combination also acts protectively on gastrointestinal and hepatic function, skin regeneration and hydration, and reduces the effects of aging, stretch marks, and pigmentation in skin. Red propolis and LC each possess low toxicity and are readily bio-accessible and bioavailable.

Turning first to the formulations described in accordance with embodiments of the invention, formulations are provided comprising a combination of propolis and LC as active ingredients. The propolis used in the combination may be green, brown, or may particularly be red propolis. More particularly, the propolis may be characterized by its chemical composition, in which its principal compounds belong to the classes of isoflavonoids (e.g., isoflavones, isoflavanes, and pterocarpanes), chalcones, and isoprenylated benzophenones. The molecules contained in the red propolis may particularly include the phenolic compounds isoliquiritigenin and liquiritigenin, the isoflavones formononetin and biochanin A, the isoflavanes vestitol, 7-O-methyl-vestitol and neovestitol, the pterocarpanes medicarpine, homopterocarpine, vesticarpane, 3,8-dihydroxy-9-methoxy-pterocarpane and 3-hydroxy-8,9-dimethoxy-pterocarpane, and the isoprenylated benzophenones guttiferone E and/or xanthochymol, guttiferone A and nemorosone, naphthoquinone epoxide, 3,4,2',3'-tetrahydroxychalcone and a flavone C-glycoside.

In one aspect, the formulation is provided as an aqueous solution or suspension. The aqueous solution or suspension may include as active ingredients red propolis at a concentration of about 0.01-1.00% mass/mass, and *L. calcareum* at a concentration of about 0.01-1.00% mass/mass. Additional inactive ingredients may include deionized water (qs), ethoxylated lanolin (Cremophor) (about 0.50-3.00% mass/mass), and sunflower oil (about 0.50-3.00% mass/mass). The aqueous preparation may be formulated using additional inactive ingredients as known in the art for use as, e.g., a spray or rinse for use in a subject's oral cavity, nasal passages, and/or sinus cavities, or as a beverage for ingestion.

In another aspect, the formulation is provided as an ingestible solid or liquid form containing the combination of propolis, e.g., red propolis, and LC. As used herein, the term ingestible refers to a solid or liquid, which may be a food, beverage, nutraceutical product, or pharmaceutical product, as known in the art, that is suitably bioavailable and non-toxic upon oral administration and ingestion by the subject. In various embodiments, the ingestible solid or liquid form may be a pharmaceutical formulation, e.g., a tablet, capsule, or liquid formulation for oral administration, e.g., a pediatric formulation. A tablet or capsule may comprise red propolis and LC as active ingredients, together with one or more pharmaceutically acceptable excipients, and may provide immediate or controlled release of the active ingredients. Still further, the active ingredients may be administered in liquid suspension or solution form, either orally or intravenously.

In still further embodiments, the solid or liquid form may be a functional food. Functional food embodiments may include solid foods, beverages, powdered beverage mixes, or beverage concentrate preparations for oral consumption. In particular, the formulation may be a candy, e.g., a hard candy, a caramel, or a gummy candy such as a gummy bear or bear-shaped candy. Such candies may contain red propolis in the form of dry or liquid ethanolic extract of red propolis, e.g., at a concentration of 0.005% to 0.02%, and LC in the form of a dry extract of LC, e.g., at a concentration of 0.01% to 0.1%. In one embodiment, the candy may be sweetened with sucrose, glucose, or a combination thereof, and may further contain starch, e.g., acid-treated modified corn starch. Sugar-sweetened candy formulations may further include additional inactive ingredients including, without limitation, citric acid, lactic acid, water, sodium citrate, gelatin, and natural food coloring and flavoring agents such as carminic acid, and strawberry and other natural flavors. In a further embodiment, the candy may be free of sugar and starch, and may instead be sweetened by oligofructose, inulin, stevioside, or a combination of two or more of the foregoing. Sugar-free candy formulations may further include additional inactive ingredients including, without limitation, citric acid, lactic acid, water, sodium citrate, gelatin, and natural food coloring and flavoring agents such as carminic acid, and strawberry and other natural flavors.

In another aspect, a topical preparation is provided containing the combination of propolis, e.g., red propolis, and LC. The topical preparation may be in the form of a serum, e.g. a serum emulsion, and may include as active ingredients LC in the form of glycolic extract of LC, e.g., in a concentration of about 0.01 to 1.0%, and glycolic extract of red propolis, e.g., in a concentration of about 0.05 to 1.0%. The serum may include as inactive ingredients, e.g., deionized water, disodium EDTA, sodium acrylates copolymer and lecithin, hyroxymethylcellulose, propylene glycol, biosaccharide gum-1/phenoxyethanol, and oat kernel extract. In some embodiments, perfuming agents may also be included.

Topical formulations containing red propolis and LC may further be in the form of creams, lotions, ointments, and other cosmetic products as known in the art. Non-limiting examples of such cosmetic products may include, e.g., lipstick, foundation, concealer, eyeliner, eye shadow, blusher, bronzer, or mascara. Such formulations may be prepared by combining the red propolis and LC-containing serum emulsion with other ingredients as known in the art. For example, such ingredients may include, without limitation and only as examples, an antibacterial agent; a sequestering agent; a powder component; or a physiologically active component. Thus, the resulting cream, lotion, ointment, or other cosmetic product has a lower concentration of LC and red propolis than the serum emulsion.

In accordance with further aspects of the invention, methods of treatment using the combination of LC and propolis, e.g., red propolis, are provided herein. As used herein, treatment may be considered to include a reduction in severity of symptoms, the prevention of progression, the prevention or avoidance of manifestation of future symptoms, or the complete resolution of one or more symptoms of the relevant disease or condition after such symptom or symptoms have manifest in the individual. The combination may be administered after the onset of at least one symptom of the disease or condition, or prior to the manifestation of symptoms in the context of prevention. Administration of the combination after the symptom or condition has begun to manifest can reduce the severity of the symptom(s), eliminate the symptom(s), prevent the progression or intensification of the symptom(s).

One such method provides for the treatment of a subject in need of treatment for a disease or condition that is responsive to a combination of LC and propolis, e.g., red propolis. As used herein, subject refers to a mammal, and may particularly refer to a human subject. The method comprises rinsing or spraying one or more of an oral cavity, a nasal passage, or a sinus cavity of the subject with an aqueous solution or suspension containing the combination of red propolis and LC. As described herein, the solution or suspension may contain red propolis as an extract of red propolis in an amount of 0.01-1.00% m/m in the aqueous solution or suspension, and LC as an extract of LC, in an amount of 0.01-1.00% m/m in the aqueous solution or suspension. This method may be useful where the disease or condition responsive to the combination of LC and red propolis is, e.g., influenza, an upper or lower respiratory infection, oral cavity inflammation, or pharynx inflammation, for example to reduce the duration or severity of symptoms, or to prevent infection or intensification of symptoms. This method may also be useful where the disease or condition responsive to the combination of LC and red propolis is cancer, e.g., head and neck cancer. In such an embodiment, treatment may act to prevent or treat head and neck cancers, e.g., through cytotoxic activity in cancer cells, reduction in proportion and proliferation of cancer stem cells, and down-regulation of the expression of key functional regulators of cancer stemness.

Another method provided herein includes the treatment of a subject in need of treatment for a disease or condition that is responsive to a combination of LC and propolis, e.g., red propolis, in which the formulation comprises the combination of red propolis and LC in an ingestible solid or liquid form. In such a method, the ingestible solid or liquid form is orally administered to subject, i.e. ingested by the subject. An exemplary ingestible solid form may include, e.g., red propolis in the form of dry ethanolic extract of red propolis (0.005% to 0.02% in the formulation); and LC in the form of a dry extract of LC (0.01% to 1.0% in the formulation). This oral administration and ingestion may produce a local or systemic effect in the subject, and may affect the progression of any disease or condition responsive to the combination of LC and red propolis. Such diseases or conditions may including, without limitation, malnutrition, influenza, flu-like infections, an upper or lower respiratory infection, oral cavity inflammation, pharynx inflammation, immune system enhancement, a gastric ulcer, colitis, gastritis, chronic diseases such as heart disease, diabetes, and hypertension, and neuronal degenerative diseases such as, e.g., Alzheimer's Disease. In further embodiments, the disease or condition responsive to the combination of LC and red propolis may be a cancer, e.g., glioblastoma, melanoma, lung cancer, prostate cancer, bladder cancer, or head and neck cancer. Treatment according to the embodiments described herein may act to prevent or treat various forms of cancer, e.g., through cytotoxic activity in cancer cells, reduction in proportion and proliferation of cancer stem cells, and down-regulation of the expression of key functional regulators of cancer sternness.

A further method provided herein includes the treatment of a subject in need of treatment for a disease or condition that is responsive to a topical preparation containing a combination of LC and propolis, e.g., red propolis. In such a method, the topical preparation is applied to an affected area of the subject's skin, for example the face, and may produce a localized effect. In various embodiments, the disease or condition responsive to the combination of LC and red propolis may be an injury such as, e.g., a wound or a burn, or may be, e.g., acne, herpes simplex or herpes genitalis, neurodermatitis, or further may be a benign but undesired condition such as, e.g., signs of aging, excessive or undesired pigmentation, stretch marks, dry skin, or skin inflammation. The disease or condition may also be any other condition known in the art to be improved antioxidant, antibacterial, antiviral, antifungal, anti-cancer, or immunomodulatory activity, as these properties are demonstrated by the formulations described herein.

In each of the foregoing methods, the combination of LC and red propolis produces a synergistic effect that is greater than the individual effects attainable via separate or sequential administration of red propolis and LC. As previously described, red propolis demonstrates marked antimicrobial activity, which complements the immunomodulatory activity of LC, and particularly the increase in SIgA levels in the oral environment and gastrointestinal tract when administered as an oral spray, rinse, or ingestible form. In particular, treatment with LC enhances oral mucosal and intestinal epithelial absorption, increases SIgA levels, and improves oral health, gut function, and gut microbial diversity. This in turn creates an environment in which the therapeutic activities attributed to red propolis (e.g., antimicrobial, anti-inflammatory, and anti-tumorigenic activities and others) are increased.

Further embodiments of the invention provide a process for preparing red propolis extract, for example, for use in the preceding formulations or methods. The process comprises extracting one or a plurality of active compounds from homogenized red propolis in a hydro-alcoholic ethanol solution at 25-28 degrees Celsius, and subjecting the homogenized material in the hydro-alcoholic ethanol solution to ultrasound for 2-3 hours. The active compounds to be extracted may include, e.g., isoprenylated benzophenones, pterocarpanes, and/or isoflavanes. In various embodiments, the hydro-alcoholic ethanol solution may include one or more of: water, an alcohol, a ketone, an ester, or an organic solvent, and the concentration of propolis in the solvent is between about 5% and about 30%, e.g., about 11%, resulting in a final concentration of 0.01% to 0.1% active compound in the hydro-alcoholic ethanol solution. The resulting red propolis extract may have a pH between about 4 and about 5, which is compatible with the pH of LC extract for use, e.g., in formulations and methods as described herein. Prior to combination with red propolis extract, the LC extract may be prepared in accordance with descriptions in U.S. Pat. No. 10,285,929. If adjustment of the pH of the red propolis extract is desired, one or more of one or more of citric acid, sodium citrate, sodium hydroxide, hydrochloric acid, or phosphoric acid may be used to adjust a pH of the resulting red propolis extract.

An additional embodiment of the invention provides for the use of a combination of *L. calcareum* and red propolis in the manufacture of a medicament for treating a disease or condition as described herein.

A further embodiment provides a combination of *L. calcareum* and red propolis for use in the treatment of a disease or condition as described herein.

EXAMPLES

The red propolis evaluated in the following working examples is characterized by its chemical composition, in which its principal compounds belong to the class of the isoflavonoids (i.e. isoflavones, isoflavanes and pterocarpanes), chalcones, and to the class of isoprenylated benzophenones. The molecules contained in the red propolis are the phenolic compounds isoliquiritigenin and liquiritigenin, the isoflavones formononetin and biochanin A, the isoflavanes vestitol, 7-O-methyl-vestitol and neovestitol, the pterocarpanes medicarpine, homopterocarpine, vesticarpane, 3,8-dihydroxy-9-methoxy-pterocarpane and 3-hydroxy-8,9-dimethoxy-pterocarpane, and the isoprenylated benzophenones guttiferone E and/or xanthochymol, guttiferone A and nemorosone, naphthoquinone epoxide, 3,4,2',3'-tetrahydroxychalcone and a flavone C-glycoside.

Example 1: Biological Activity

Head and neck squamous cell carcinoma cell lines, UM-SCC-17B (laryngeal cancer (metastasis)) and UM-SCC-74A (base of tongue (primary tumor)) are cultured in Dulbecco's Modified Eagle Medium (DMEM, Invitrogen; Grand Island, N.Y., USA), supplemented with 10% fetal bovine serum (FBS) (Invitrogen) and with 100 U/ml penicillin-streptomycin (Invitrogen). The identity of all tumor cell lines is confirmed by genotyping at the University of Michigan DNA sequencing core facility. Human dermal microvascular endothelial cells (HDMEC; Lonza, Walkersville, Md., USA) are cultured in endothelial cell growth medium-2 (EBM2; Lonza), supplemented with hEGF, hydrocortisone, GA-1000 (Gentamicin, Amphotericin-B), 5% FBS, VEGF, hFGF-B, R3-IGF-1, and ascorbic acid (EGM2-MV Bulletkit). *Mycoplasma* Detection Kit (Plasm® Test®, InvivoGen, San Diego, Calif., USA) is performed to ensure that all cell lines are *mycoplasma*-free.

The propolis is typified by high-performance liquid chromatography (HPLC) in which prenylated compounds, cinnamic acid derivatives and flavonoids are detected as the main constituents for brown and green propolis, whereas the main constituents for red propolis are antioxidants. Natural raw propolis is extracted in dimethyl sulfoxide (DMSO) by shaking for three days at 37° C. The resulting solution is centrifuged at 13,000 rpm for 5 minutes at 25° C. and filtered through a 0.22 µM strainer. The propolis solution is named Extract of Propolis in DMSO (EPDMSO). Experimental groups are, as follows: vehicle control (DMSO); 0.5 µg/ml, 5.0 µg/ml, and 50 µg/ml (EPDMSO).

In Example 1, means±standard deviation (SD) of three independent experiments are calculated. One-way ANOVA followed by post-hoc tests (Tukey) are performed using the SigmaStat 16.0 software (SPSS, Chicago, Ill.). Statistical significance is determined at $p<0.05$.

Example 1.1: Cytotoxicity Assay; Comparative Effects of Red, Brown, and Green Propolis on Cell Density Methods: A sulforhodamine B (SRB) assay is performed to evaluate the effect of green, brown, and red propolis on proliferation of stem cells of head and neck squamous cancer cells (HNSCC), and to evaluate the effect of propolis on cell viability. In the study, cells of squamous carcinoma cell lines UM-SCC-17B (laryngeal cancer (metastasis)), UM-SCC-74A (base of tongue (primary tumor)), and Human Dermal Microvascular Endothelial Cells (HDMEC) are seeded at $2\times10^4$ cells per well in 96-well plates, allowed to attach overnight, and treated with control vehicle (DMSO), 0.5 µg/ml, 5.0 µg/ml, and 50 µg/ml EPDMSO of each of green, brown and red propolis for 72 hours. Cells are fixed using 10% trichloroacetic acid, stained with 0.4% SRB (Sigma-Aldrich) in 1% acetic acid, and plates are read to assess cell viability in a microplate reader at 560 nm (GENios; Tecan, Männedorf, Switzerland). Data are obtained from triplicate wells/condition and represent 3 independent experiments.

Results: Results are illustrated in FIGS. 1A-1I. As shown in FIG. 1A-1F, treatment with red, brown, and green propolis at 50 µg/ml markedly reduces cell density in UM-SCC-17B and UM-SCC-74A cells after 72 hours of treatment, compared to treatment with red, brown, and green propolis at lower concentrations (0.5 µg/ml and 5.0 µg/ml) and compared with vehicle control. Treatment with red, brown, and green propolis at 50 µg/ml also demonstrates an inhibitory effect on the density of HDMEC cells (FIG. 1G-1I). Among extracts of red propolis (FIGS. 1A, 1D, 1G), brown propolis (FIGS. 1B, 1E, 1I), and green propolis (FIGS. 1C, 1F, 1I), extract of red propolis shows the greatest impact on cell viability during the experimental period.

Figure 1D:
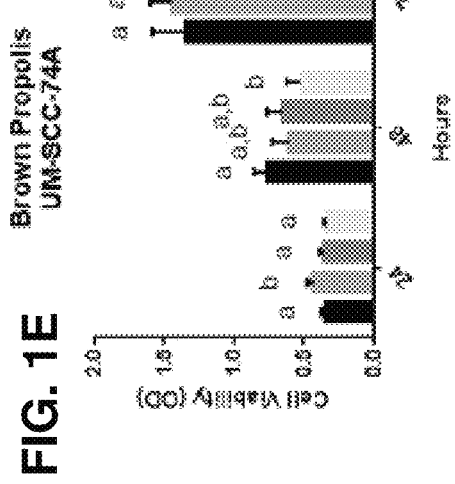
FIG. 1D is a bar chart illustrating the effect on UM-SCC-74A cell viability over time following administration of vehicle, 0.5 μg/ml, 5.0 μg/ml, and 50 μg/ml of red propolis, respectively.
Figure 1E:
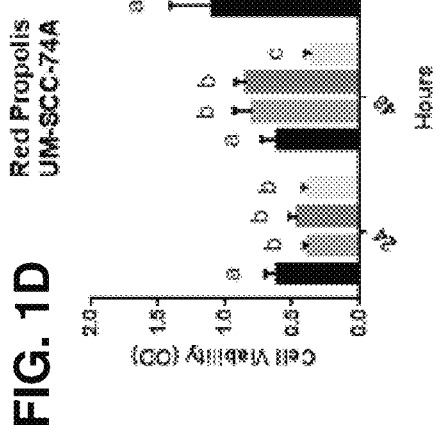
FIG. 1E is a bar chart illustrating the effect on UM-SCC-74A cell viability over time following administration of vehicle, 0.5 μg/ml, 5.0 μg/ml, and 50 μg/ml of brown propolis, respectively.
Figure 1F:
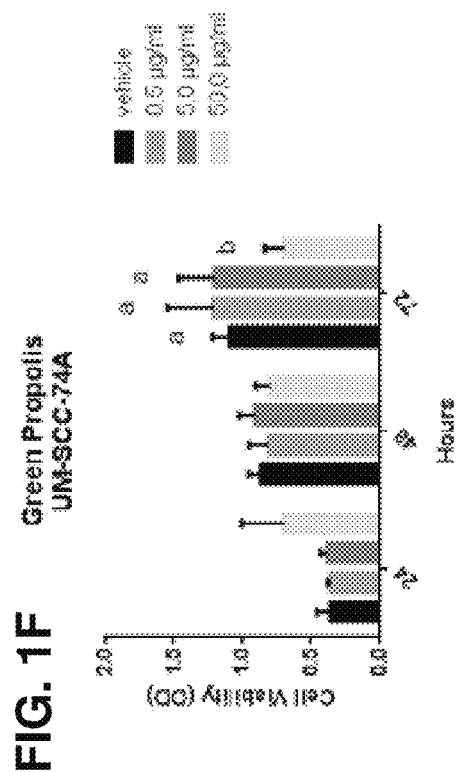
FIG. 1F is a bar chart illustrating the effect on UM-SCC-74A cell viability over time following administration of vehicle, 0.5 μg/ml, 5.0 μg/ml, and 50 μg/ml of green propolis, respectively.

In FIGS. 1A-1I, different lower case letters (a, b, c) indicate statistical difference (p<0.05). For example, in FIG. 1A, at each of 48 hours and 72 hours, a statistically significant difference in cell viability (p<0.05) exists between (a) vehicle, 0.5 µg/ml red propolis EPDMSO, and 5.0 µg/ml red propolis EPDMSO; and (b) 50 µg/ml red propolis EPDMSO. In FIG. 1D, at 24 hours a statistically significant difference in cell viability (p<0.05) exists between (a) vehicle; and (b) 0.5 µg/ml red propolis EPDMSO, 5.0 µg/ml red proplis EPDMSO, and 50 µg/ml red propolis EPDMSO; at 48 hours statistically significant differences in cell viability (p<0.05) exist between each of (a) vehicle; (b) 0.5 µg/ml red propolis EPDMSO and 5.0 µg/ml red propolis EPDMSO; and (c) 50 µg/ml red propolis EPDMSO. The (a), (b), and (c) indicators of statistical significance have analogous meanings throughout FIG. 1A-1I. The results suggest an anti-tumor angiogenesis effect of red propolis on the cell lines tested. On the basis of its more significant effect, red propolis EPDMSO is selected for use in studies described in Examples 1.2 and 1.3.

Example 1.2: Western Blot Assays; Stemness of HNSSC Cells

Figure 2A:
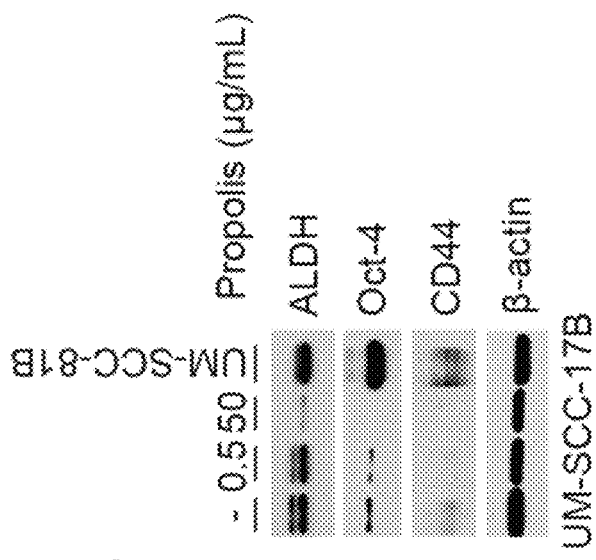
FIG. 2A illustrates a Western blot for ALDH, Oct-4, and CD44 in UM-SCC-17B cells exposed to red propolis (5.0 m/ml) or vehicle control for 24-72 hours.
Figure 2B:
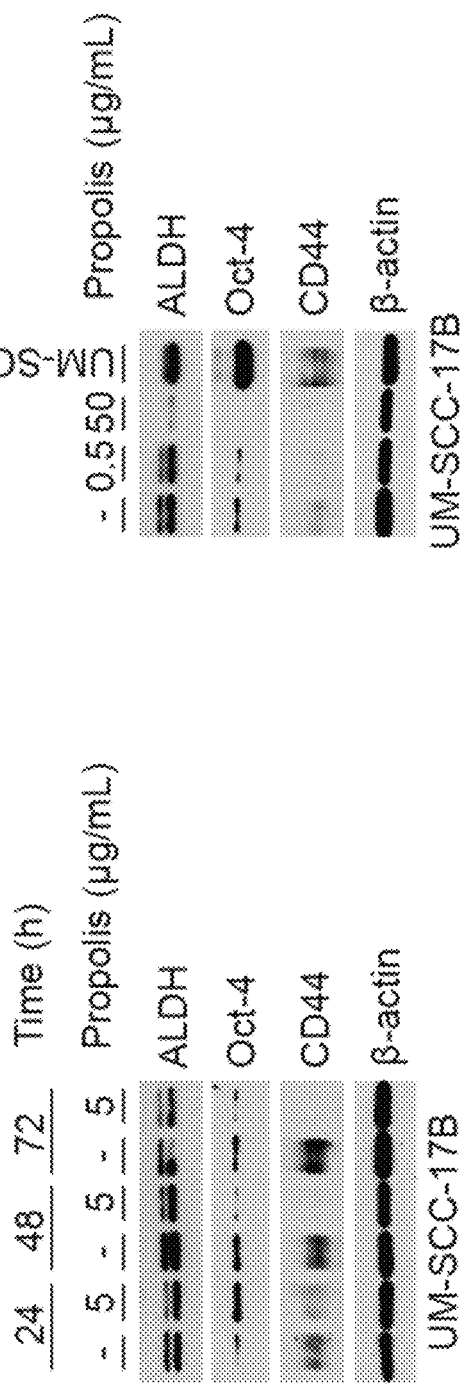
FIG. 2B illustrates a Western blot for ALDH, Oct-4, and CD44 in UM-SCC-17B cells exposed to increasing concentrations of red propolis (0.5, 5.0, and 50 μg/ml) for 24 hours. UM-SCC-81B is used as a positive control.
Figure 2C:
FIG. 2C illustrates a Western blot for Bmi-1 in UM-SCC-17B cells exposed to red propolis (5 μg/ml) or vehicle control for 24-72 hours.
Figure 2D:
FIG. 2D illustrates a Western blot for Bmi-1 in UM-SCC-17B cells exposed to increasing concentrations of red propolis (0.5, 5.0, and 50 μg/ml) for 24 hours. UM-SCC-81B is used as a positive control.

Methods: To evaluate the effect of red propolis on the stemness of head and neck cancer cells (squamous carcinoma cell line UM-SCC-17B), western blot assays are performed to determine the expression of key cancer stem cell markers (e.g. ALDH, CD44) and stem cell/self-renewal markers (e.g. Oct-4, BMI-1). UM-SCC-17B cells are treated with 0.5 µg/ml and 50 µg/ml red propolis EPDMSO for 24 hours (FIGS. 2B and 2D). Alternatively, cells are exposed to 5.0 µg/ml red propolis EPDMSO or vehicle control for 24, 48, or 72 hours (FIGS. 2A and 2C). Primary antibodies are as follows: rabbit anti-human Bmi-1 or Oct-4 (Cell Signaling Technology); mouse anti-human CD44 (Cell Signaling Technology), ALDH1/2 (Santa Cruz Biotechnology) or β-actin (Chemicon/Millipore). Immunoreactive proteins are visualized by SuperSignal West Pico chemiluminescent substrate (Thermo Scientific). UM-SCC-81B, a HNSSC cell line known to express high constitutive levels of ALDH, Oct-4 and CD44, is used as a positive control (FIG. 2B).

Results: Results are shown in FIGS. 2A-2D. Treatment with red propolis down-regulates the expression of ALDH, CD44, Oct-4 and BMI-1 in a time-dependent (FIGS. 2A and C) and dose-dependent manner (FIGS. 2B and D). 5.0 µg/ml red propolis EPDMSO shuts down the expression of CD44 and BMI-1 after 48 hours of treatment (FIGS. 2A and C). These results suggest a role of red propolis in the regulation of critical stemness regulators in HNSCC cells, and superior effects of red propolis on curtailing the proliferation of stem cells of HNSCC.

Example 1.3: Cell Sorting for CD44/ALDH; Orosphere Assay

An orosphere assay provides an in vitro method for studying head and neck cancer stem cells (CSCs), while allowing for the propagation of CSC that retain stemness and self-renewal properties. $ALDH^{high}CD44^{high}$ cells have a higher capacity to form orospheres when compared to $ALDH^{high} CD44^{low}$ cells.

Methods: Single cell suspensions are obtained from trypsinization of UM-SCC-17B cells after treatment for 24 hours and re-suspended at $1\times10^6$ cells/ml PBS. Aldefluor kit (Stem Cell Technologies; Vancouver, Canada) is used to identify ALDH activity. Cells are incubated with activated Aldefluor substrate (BAA) or the ALDH inhibitor (DEAB) for 45 minutes at 37° C. Then, cells are exposed to anti-CD44 antibody (clone G44-26BD; BD Pharmingen; Franklin Lakes, N.J., USA). 7-Aminoactinomycin (7-AAD, BD Pharmingen) is used to select viable cells, and a flow cytometry assay is carried out to sort the CSC (i.e. $ALDH^{high}CD44^{high}$) cells and non-CSC (i.e. $ALDH^{low}CD44^{low}$) cells. Orospheres (i.e. non-adherent spheroids formed by ≥25 HNSCC cells) are generated from 1,500 sorted cells in 6-wells ultra-low attachment plates (Corning, N.Y., USA). Cells ($ALDH^{high}CD44^{high}$ or $ALDH^{low}CD44^{low}$) are plated immediately after sorting and maintained in low glucose DMEM, 10% FBS (Invitrogen), and 100 U/ml Penicillin-streptomycin (Invitrogen) overnight before treatment. $ALDH^{high}CD44^{high}$ cells are treated with increasing concentrations of red propolis EPDMSO (0.5, 5.0, and 50 µg/ml) for 10 days. Alternatively, $ALDH^{high}CD44^{high}$ and $ALDH^{low}CD44^{low}$ sorted cells are plated as single cells in 96-well plates and exposed to 5.0 µg/ml red propolis EPDMSO or vehicle control for 10 days. This experimental design (i.e. single cell assay) avoids cell aggregation, as CD44 is a molecule involved in cell adhesion. New media and treatment are added every four days. At the completion of the experimental period, orospheres are counted under light microscope. Data are obtained from triplicate wells/condition and represent three independent experiments.

Figure 3B:
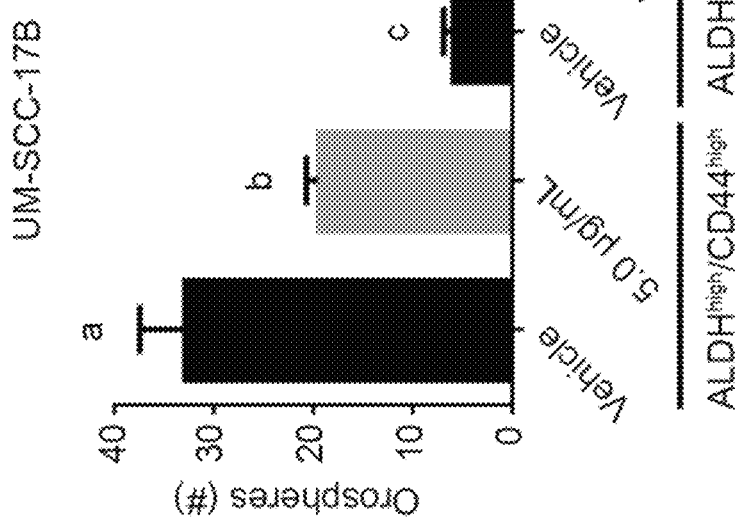
FIG. 3B is a bar chart showing the effect of 5.0 μg/ml red propolis treatment compared to vehicle control on the number of orospheres formed by $ALDH^{high}CD44^{high}$ or $ALDH^{low}CD44^{low}$ cells.
Figure 3A:
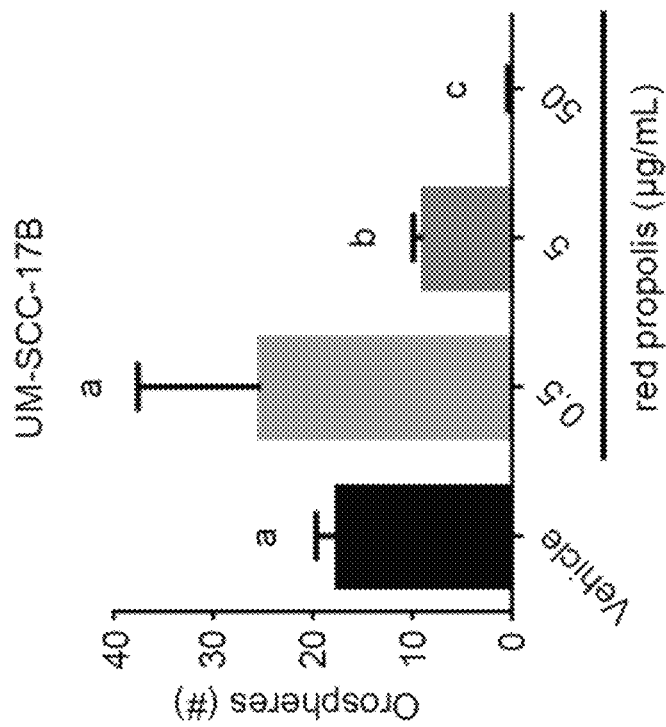
FIG. 3A is a bar chart showing the effect of red propolis treatment (0.5, 5.0, and 50 μg/ml) compared to vehicle control on the number of orospheres formed by UM-SCC-17B sorted cells ($ALDH^{high}CD44^{high}$).

Results: As shown in FIG. 3A, red propolis EPDMSO (5.0 or 50 µg/ml) causes a significant reduction in the number of orospheres as compared with 0.5 µg/ml propolis or vehicle control (p<0.05). No orospheres are observed with 50 µg/ml red propolis EPDMSO. As shown in FIG. 3B, $ALDH^{low}CD44^{low}$ cells form fewer orospheres than $ALDH^{high}CD44^{high}$ cells. FIG. 3B further shows that after 10 days, red propolis EPDMSO significantly reduces the number of orospheres formed by $ALDH^{high}CD44^{high}$ cells compared to treatment with vehicle control (p<0.05). Taken together, these results indicate that red propolis reduces the viability of head and neck cancer stem cells.

The foregoing results demonstrate that red propolis not only reduces the proportion of CSC, but also downregulates the expression of key functional regulators of cancer stemness. Moreover, this red propolis is cytotoxic to HNSCC cells, suggesting a potential role of propolis as an adjuvant agent for prevention and treatment of head and neck cancer.

Example 2: Formulations

The formulations described herein are developed containing a combination of red propolis and red algae (*L. calcareum*). Previously, an alcoholic extract of red propolis with high content of phenolic substances was elaborated as follows: 30 g of crushed propolis was extracted with 100 mL of ethanol in agitation at 40° C. for 24 hours. The material was then filtered, and the filtrate was dried under vacuum in a rotary evaporator. The dry extract (EEP) was kept in a container away from light, until its use. Aqueous solution, functional food, and topical formulations containing the combination of red propolis and red algae (*L. calcareum*) are described herein.

Example 2.1: Aqueous Formulation of Red Propolis and *L. Calcareum*

The aqueous solution described herein associates a dry ethanol extract of red propolis and a dry extract of red algae. The aqueous solution is prepared using the following method and amounts as provided in table 1 below.

Weigh all ingredients separately. Add propolis and algae extracts. Gradually add sunflower oil until it forms a paste. Then add little by little to the ethoxylate lanolin until homogenized well. When everything is well mixed, add the water very slowly. Store away from light.

TABLE 1

| Aqueous solution | |
|---|---|
| DESCRIPTION | 100% (mass/mass) |
| Deionized water | QS* |
| Ethanol extract of red propolis | 0.01-1.00 |
| Glycolic extract of red algae | 0.01-1.00 |
| ethoxylated lanolin (Cremophor) | 0.50-3.00 |
| Sunflower oil | 0.50-3.00 |

*Quantum satis

The aqueous solution as described herein is useful as a platform for other solutions including, e.g, oral or nasal spray or rinse.

Example 2.2: Red Propolis and LC Functional Food Formulation

Example 2.2.1: Sugar-Containing Candy

A hard candy, caramel, or gummy candy (e.g. gummy bear) containing sugar and starch is prepared incorporating a dry ethanol extract of red propolis (free of alcohol) and dry extract of *L. calcareum*. Natural food coloring, e.g., carminic acid, and strawberry aroma, also natural, are used. The sugar-containing candy is prepared according to the following method and amounts as shown in table 2.

Gelatin is hydrated in water, immersed in a hot water bath, and stirred until completely diluted. The gelatin is reserved in the hot bath until later use. Sucrose and glucose syrup are mixed and then the starch added (dissolved in water), leaving the mixture boiling at controlled temperature until the starch is cooked.

Preparation of additional ingredients: after weighing the ingredients in smaller amounts, those in a powder format are dissolved in water and reserved for later use. Then, the remaining ingredients are added to the sucrose, glucose syrup, starch, and gelatin mixture, and the mixture is homogenized, resulting in a homogeneous matrix. Brix degrees are measured, and the mixture is deposited in trays with corn starch powder molds, previously conditioned in a climatic chamber. For drying, candy is kept in climatic chambers with circulating air and then taken from the mold. Hedonistic assays are performed with untrained panelists with significant acceptance.

TABLE 2

| Sugar-containing candy | |
|---|---|
| DESCRIPTION | 100% (m/m) |
| Starch (acid-treated modified corn starch) | 5.00-12.00 |
| Citric acid | 1.00-2.00 |
| Lactic acid | 0.50-1.00 |
| Water | 8.00-12.00 |
| Strawberry scent | 0.10-1.00 |
| Sodium citrate | 0.05-0.20 |
| Carminic dye (carminic acid) | 0.01-1.00 |
| Dry extract of red algae | 0.01-1.0 |
| Dry extract of red propolis | 0.005-0.02 |
| Gelatin Type A | 2.00-4.00 |
| Sucrose | 17.00-25.00 |
| Glucose syrup (glucose) | 35.00-45.00 |

Example 2.2.2: Sugar/Starch-Free Candy

A hard candy, caramel, or gummy candy (e.g. gummy bear) containing no sugar or starch, and containing as a sweetener *stevia* and inulin, is prepared by incorporating a dry ethanol extract of red propolis (free of alcohol) and a dry extract of *L. calcareum*. The sugar-free candy is prepared according to the following method and amounts as shown in table 3.

Gelatin is hydrated in water, immersed in a hot water bath, and stirred until completely diluted. The gelatin is reserved in the hot bath until later use. Inulin powder is gradually added to FOS syrup and homogenized with a mixer until a cream is obtained, and kept for later use. Preparation of additional ingredients: after weighing the ingredients in smaller amounts, those in a powder format are dissolved in water and reserved for later use. Inulin cream and gelatin are added at a controlled temperature, with slow agitation until dissolved. Then, the remaining ingredients are added to the inulin and gelatin mixture, and the mixture is homogenized, resulting in a homogeneous matrix. Brix degrees are measured, and the mixture is deposited in trays with corn starch powder molds, previously conditioned in a climatic chamber. For drying, candy is kept in climatic chambers with circulating air and then taken from the mold.

Hedonistic assays are performed with untrained panelists with significant acceptance.

TABLE 3

| Sugar-free candy | |
|---|---|
| DESCRIPTION | 100% (m/m) |
| Citric acid | 1.00-2.00 |
| Lactic acid | 0.50-1.00 |
| Water | 8.00-12.00 |

TABLE 3-continued

Sugar-free candy

| DESCRIPTION | 100% (m/m) |
|---|---|
| Strawberry scent | 0.10-1.00 |
| Sodium citrate | 0.05-0.20 |
| Carminic dye (carminic acid) | 0.01-1.00 |
| Dry extract of red algae | 0.01-1.0 |
| Dry extract of red propolis | 0.005-0.02 |
| FOS P95 (oligofructose) | 65.00-85.00 |
| Gelatin type A | 2.00-4.00 |
| Inulin (Chicory) | 8.00-15.00 |
| Stevioside | 0.10-0.20 |

Example 2.3: Topical Preparations Containing *L. Calcareum* and Red Propolis

A serum formulation containing red propolis and *L. calcareum* (LC) is prepared as described. Red propolis is extracted using an extraction solvent selected from water, an alcohol, a ketone, an ester and/or an organic solvent. The pH of the resulting extract is in the range of 4 to 5 and is compatible with the pH of LC extract. Citric acid, sodium citrate, sodium hydroxide, hydrochloric acid, phosphoric acid, and others may be used for pH adjustment as needed. The combined extracts of red propolis and LC produce an oily raw material, which is blended with any of a surfactant, a moisturizer, a thickener polymer, a film polymer, an ultraviolet absorber, an oxidation agent, an antibacterial agent, a sequestering agent, a powder component, a physiologically active component, depending on the specific cosmetic product to be formulated, as long as the effects of the present invention are not impaired. The cosmetic product may be a facial cream, lotion, emulsion, cream, oil, ointment, lipstick, foundation, eyeliner, blusher, mascara, etc. An exemplary formulation for a serum emulsion that can be used in various vehicles is provided in Table 4.

TABLE 4

Serum emulsion formulation

| DESCRIPTION | Percentage by mass |
|---|---|
| Deionized water | QS* |
| Disodium EDTA (EDTA Na₂) | 0.10% |
| LECIGEL sodium acrylates copolymer and lecithin | 0.04% |
| CELLOSIZE QP-100 hydroxyethyl cellulose | 0.5% |
| Propylene glycol | 1.00% |
| FUCOGEL Biosaccharide gum-1/phenoxyethanol | 2.00% |
| OSILIFT Avena sativa (oat) kernel extract | 2.0% |
| Glycolic extract of LC | 0.01-1.0% |
| Glycolic extract of red propolis | 0.05-1.0% |
| Essence (parfum) | 0.3% |
| Total | 100% |

*Quantum satis

OSILIFT BIO is a natural polyoses purified fraction obtained from oats issued from organic farming. This compound is useful for dermatological applications due to the tridimensional configuration and high molecular weight configuration, and creates an immediate lifting, smoothing, or tensor effect visible on the skin surface.

FUCOGEL 1.5P is an anionic polysaccharide with a high molecular weight obtained by bacterial fermentation from non-GMO vegetable substrates. It contains L-fucose, D-galactose and galacturonic acid and is used in the form of a solution at 1% (w/w) in water. FUCOGEL is a universal and multifunctional reference in the cosmetic industry, and functions to hydrate skin due to its capacity to form a film and retain water molecules. It was recently demonstrated that it activates the sirtuin-1 enzyme (NAD-dependent deacetylase sirtuin-1), a protein that in humans is encoded by the SIRT1 gene. SIRT1 stands for sirtuin (silent mating type information regulation 2 homolog) 1 (*S. cerevisiae*) and is an enzyme that deacetylates proteins that contribute to cellular regulation (reaction to stressors, longevity).

LECIGEL is phospholipid-based gelling agent which provides emulsifying properites of lecithin with thickening and texturizing effects of a polymer. LECIGEL does not contribute stickiness to the formulation and enhances hydration and bioavailability of active ingredients such as red propolis and LC.

As used herein, the terms "a" and "an" do not denote a limitation of quantity, but rather denote the presence of at least one of the referenced items. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals).

While various embodiments are described herein, it will be appreciated from the specification that various combinations of elements, variations or improvements therein may be made by those skilled in the art and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended embodiments.

What is claimed is:

1. A formulation comprising: a combination of red propolis and *L. calcareum* (LC) as active ingredients, wherein the red propolis is present as an ethanolic extract of red propolis and the LC is present as a glycolic extract of LC.

2. The formulation of claim 1, in the form of an aqueous solution or suspension, wherein the red propolis is present in an amount of 0.01-1.00% m/m in the aqueous solution or suspension, and the LC is present in an amount of 0.01-1.00% m/m in the aqueous solution or suspension.

3. The formulation of claim 2, further comprising water, sunflower oil, and ethoxylate lanolin as inactive ingredients.

4. The formulation of claim 2, in the form of an oral or nasal spray or rinse.

5. The formulation of claim 1, in ingestible solid or liquid form.

6. The formulation of claim 5, wherein the ingestible liquid form is a beverage or a beverage concentrate preparation.

7. The formulation of claim 5, wherein the ingestible solid form is a tablet, a capsule, a functional food, a powdered beverage mix, or a candy.

8. The formulation of claim 7, in the form of a candy, wherein the red propolis is present in the form of dry ethanolic extract of red propolis, and at a concentration of 0.005% to 0.02% in the formulation; and wherein the LC is present in the form of a dry extract of LC, and at a concentration of 0.01% to 1.0% in the formulation.

9. The formulation of claim 8, further comprising:
a sweetener selected from the group consisting of: sucrose, glucose, and a combination thereof; and starch.

10. The formulation of claim 8, further comprising:
one or more sweetener selected from the group consisting of: stevioside, oligofructose, and inulin.

11. The formulation of claim 1, in the form of a serum, wherein the red propolis is present as an extract of red propolis, in an amount of 0.05-1.00% m/m in the topical preparation, and
the LC is present as an extract of LC, in an amount of 0.01-1.00% m/m in the topical preparation.

12. The formulation of claim 11, further comprising:
deionized water;
disodium EDTA;
sodium acrylates copolymer and lecithin;
hyroxymethylcellulose;
propylene glycol;
biosaccharide gum-1/phenoxyethanol;
oat kernel extract;
glycolic extract of LC; and
glycolic extract of red propolis.

13. The formulation of claim 1, in the form of a cream, a lotion, an ointment, or a cosmetic product, wherein
the red propolis is present in a concentration of less than about 0.05 to about 1.0%,
the LC is present in a concentration of less than about 0.01 to about 1.0%,
and wherein the formulation further comprises:
deionized water;
disodium EDTA;
sodium acrylates copolymer and lecithin;
hyroxymethylcellulose;
propylene glycol;
biosaccharide gum-1/phenoxyethanol; and
oat kernel extract.

14. The formulation of claim 13, further comprising:
one or more additional ingredient selected from: an antibacterial agent, a sequestering agent, a powder component, and a physiologically active component.

15. The formulation of claim 14, in the form of a cosmetic product, wherein the cosmetic product is selected from the group consisting of: lipstick, foundation, concealer, eyeliner, eye shadow, blusher, bronzer, and mascara.

16. A method of treating a subject in need of treatment for a disease or condition responsive to a combination of *L. calcareum* (LC) and red propolis, the method comprising:
administering to the subject the combination of red propolis and LC according to claim 1.

17. The method of claim 16, wherein the administering comprises rinsing or spraying one or more of an oral cavity, a nasal passage, or a sinus cavity of the subject with an aqueous solution or suspension containing the combination of red propolis and LC, and
wherein the disease or condition responsive to the combination of LC and red propolis is selected from the group consisting of influenza, an upper or lower respiratory infection, oral cavity inflammation, pharynx inflammation, and a cancer of the subject's head and/or neck.

18. The method of claim 16, wherein the administering comprises orally administering an ingestible solid or liquid containing the combination of red propolis and LC to the subject,
wherein the disease or condition responsive to the combination of LC and red propolis is selected from the group consisting of: malnutrition, influenza, an upper or lower respiratory infection, oral cavity inflammation, pharynx inflammation, immune system enhancement, a gastric ulcer, colitis, gastritis, glioblastoma, melanoma, lung cancer, prostate cancer, bladder cancer, and a cancer of subject head and/or neck.

19. The method of claim 16, wherein the administering comprises applying to the subject's skin a topical preparation containing the combination of red propolis and LC, and
wherein the disease or condition responsive to the combination of LC and red propolis is selected from the group consisting of: a wound, a burn, acne, herpes simplex, herpes genitalis, neurodermatitis, aging skin, pigmented skin, dry skin, and skin inflammation.

20. The method of claim 16, wherein the disease or condition responsive to the combination of LC and red propolis is improved by one of antioxidant activity, antibacterial activity, antiviral activity, antifungal activity, anticancer activity, anti-angiogenesis activity, or immunomodulatory activity of the combination.

* * * * *